United States Patent [19]

Tackie et al.

[11] Patent Number: 5,362,726
[45] Date of Patent: Nov. 8, 1994

[54] COMPOUND AND METHOD OF TREATMENT FOR FALCIPARUM MALARIA

[75] Inventors: Albert Tackie, Manpong-Akwapin, Ghana; Paul L. Schiff, Pittsburgh, Pa.

[73] Assignees: Healthsearch, Inc., Plano, Tex.; Center for Scientific Research Into Plant Medicine, Ghana

[21] Appl. No.: 17,170

[22] Filed: Feb. 12, 1993

[51] Int. Cl.$^5$ .................. A61K 31/55; C07D 471/22
[52] U.S. Cl. .................................. 514/214; 514/215; 540/453
[58] Field of Search ................ 540/453; 514/214, 215

[56] References Cited

U.S. PATENT DOCUMENTS 4,164,499  8/1979  Rossetti et al. ................ 540/453

*Primary Examiner*—Robert T. Bond
*Attorney, Agent, or Firm*—Sherman and Shalloway

[57] ABSTRACT

This invention deals with the spirononacyclic indoloquinoline alkaloid known as cryptospirolepine and its use as an anti-malarial.

15 Claims, 9 Drawing Sheets

FIG. 6C
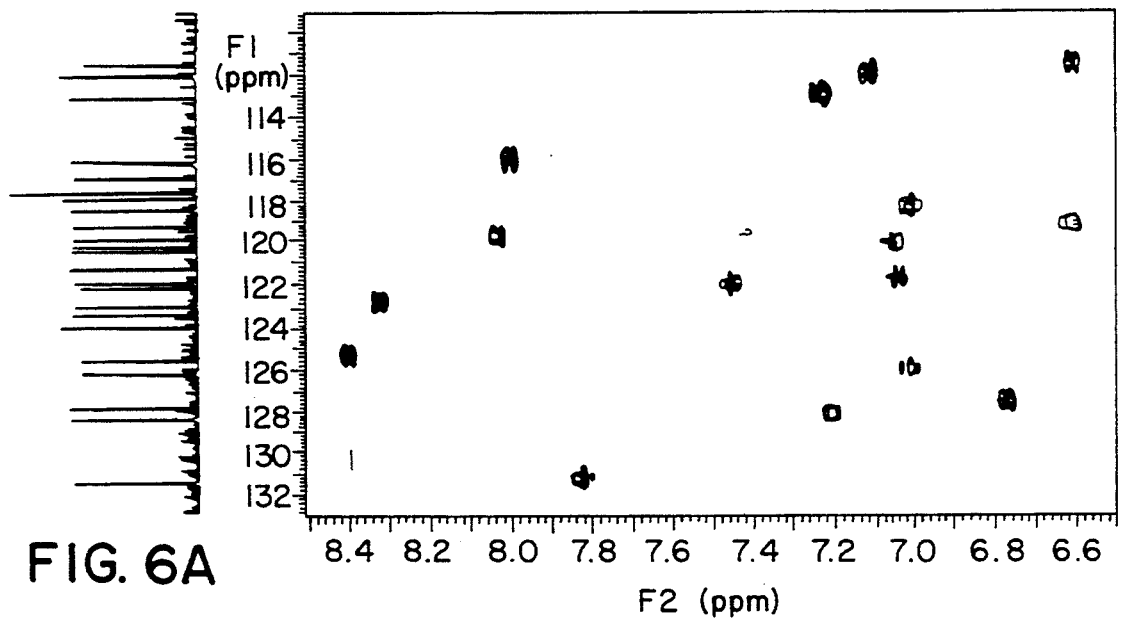
FIG. 6A
FIG. 6B

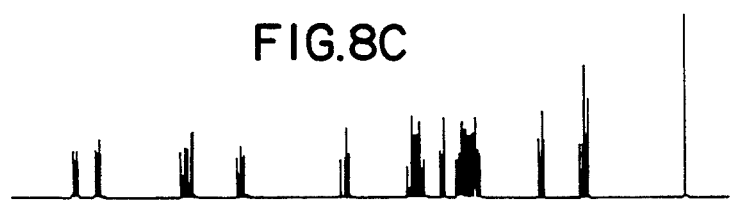
FIG.8C
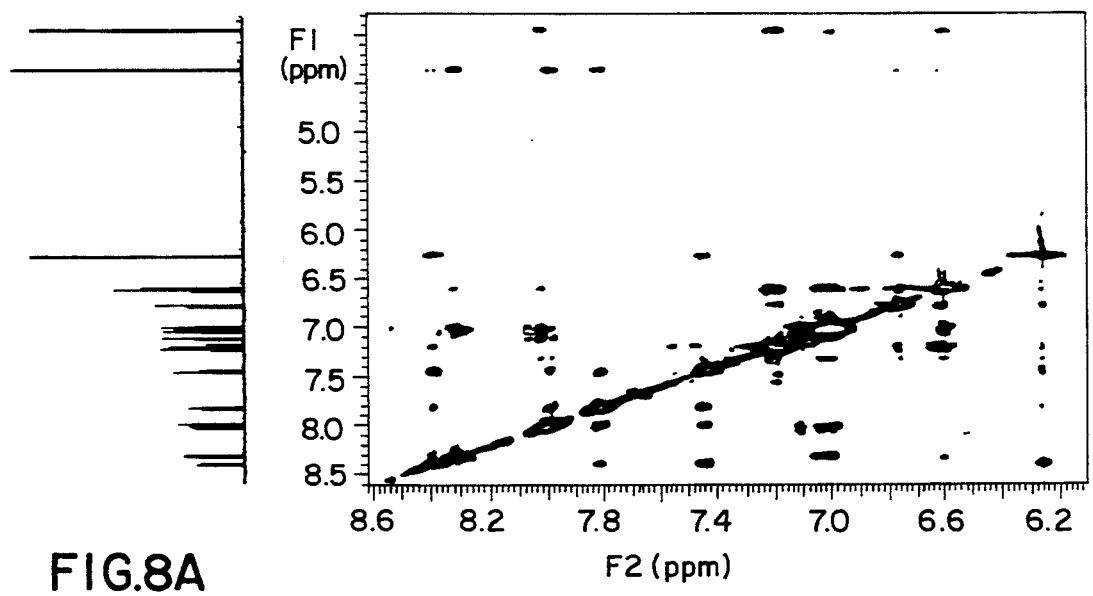
FIG.8A
FIG.8B

COMPOUND AND METHOD OF TREATMENT FOR FALCIPARUM MALARIA

FIELD OF THE INVENTION

This invention relates to a compound and method for treating patients who have been exposed to or are suffering from *falciparum* malaria. More particularly, the invention relates to the use of a spirononacyclic indoloquinoline alkaloid obtained from an extract of roots of *Cryptolepis sanguinolenta*, the latter being used in the treatment of malaria. The spirononacyclic indoloquinoline alkaloid, known as cryptospirolepine, has antimalarial effects against well characterized clones of falciparum malaria parasites.

BACKGROUND OF THE INVENTION

The most debilitating and fatal form of malaria is caused by the complex protozoan parasite, *Plasmodium falciparum*. Resistance to available drugs for the treatment of malaria was first recognized in the United States during the Vietnam conflict and has since been shown to be increasing in geographical range, severity, and prevalence. Laboratory and epidemiological evidence now suggest that *Plasmodium falciparum* has acquired multiple drug resistance that is largely independent of the chemical class of drugs to which the parasites are exposed. With multiple drug resistance in falciparum malaria coupled with an increase in worldwide tourism, the prevention and treatment of malaria is rapidly emerging as a major health issue in the United States. Consequently, it is of critical importance to develop new drugs for the treatment of *falciparum* malaria.

*Cryptolepis sanguinolenta*, a shrub indigenous to West Africa, has been used by Ghanaian traditional healers for many years for the treatment of fevers, including malaria. (Boye, G L and Ampofo, O., Proceedings of the First International Symposium on Cryptolepine, Univ. of Sci. and Tech, Kumasi, Ghana (1983)). A root decoction of Cryptolepis has been used clinically by Oku Ampofo at the Centre for Scientific Research into Plant Medicine since 1974 for the treatment of malarial fever, as well as for the treatment of bacterial infections (Boye, G L and Ampofo, O. Proceedings of the First International Symposium on Cryptolepine, Univ. of Sci. and Tech, Kumasi, Ghana (1983)).

There is sufficient evidence to suggest that the root extracts of Cryptolepis have antipyretic, antibacterial and antimalarial activity. However, the antimalarial component or components of the Cryptolepis extract are unknown.

In 1978, Dwuma-Badu, et al. isolated two alkaloids, cryptolepine and quindoline, from the roots of the West African plant *Cryptolepis sanguinolenta*. This began a series of investigations into the constituents of *C. sanguinolenta* (Dwuma-Badu, et al. (1978) J. Pharm. Sci. 67: 433–434). Cryptolepine had previously been synthesized (Fichter, F. and Boehringer, F. (1906) Ber. Dtsch. Chem. Ges. 39: 3932-3942) and chemically analyzed. Biological evaluation of cryptolepine has demonstrated that the alkaloid possesses antimicrobial, antipyretic, antiinflammatory, and hypotensive properties (Boakye-Yiadom, K. and Heman-Ackah, S. M. (1979), J. Pharm. Sci. 68: 1510–1514; Bamgbose, S.O.A. and Noamesi, B. K. (1981) Planta Med. 41: 392–396; Raymond Hamet (1937) C.R. Soc. Biol., 126: 768–770; Noamesi, B. K. and Bamgbose, S.O.A. (1980) Planta Med., 39: 51–56).

A report by Peters in 1981 indicated that cryptolepine had positive activity against rickettsia-like organisms but failed to support the clinical evidence of the antimalarial activity of the Cryptolepis extract (quoted in Boye, G L and Oku Ampofo (1983) on page 37.

Use of the crude extract for the treatment of malaria is inefficient, unreliable, and cumbersome. It also has the significant disadvantage of involving the culture and manipulation of a West African plant, rather than the utilization of an isolated pure, active component.

SUMMARY OF THE INVENTION

The present inventors have isolated, purified and characterized a novel antimalarial component from an extract of roots of the West African plant, *Cryptolepis sanguinolenta* and have named the component cryptospirolepine. Cryptospirolepine is an indoloquinoline-indolobenzazepine spiro-nonacyclic dimeric alkaloid compound having the structure

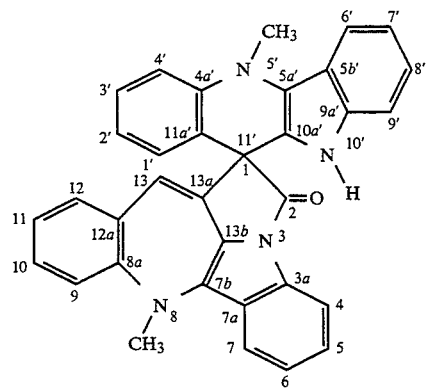

Cryptospirolepine and its acid salt are antimalarial compounds that have the ability to inhibit the growth of *Plasmodium falciparum*.

In a second aspect of the invention, the invention relates to an antimalarial composition comprising a therapeutically effective amount of cryptospirolepine and a pharmaceutically acceptable carrier. In a preferred embodiment, the antimalarial composition comprises the HCl salt of cryptospirolepine. In another preferred embodiment, the antimalarial composition further comprises an agent selected from other antimalarial agents, antibacterial agents and antipyretic agents. Acetaminophen (paracetamol) is a preferred antipyretic agent of the composition and cryptolepine, or cryptolepine-HCl are preferred additional antimalarial agents.

In another aspect of the invention, there is provided a method of treating malaria comprising the administration of a therapeutically effective amount of a composition comprising a therapeutically effective amount of cryptospirolepine or a pharmaceutically acceptable salt thereof to a patient who might be exposed to or is suffering from malaria. In a preferred embodiment, the method for treating malaria comprises the administration of a compound comprising cryptospirolepine-HCl, and other antimalarial agents, antibacterial agents and/or antipyretic agents.

In one aspect, the method for treating malaria provides for the administration of the antimalarial composition in tablet form. The composition may be administered daily.

In another aspect of the invention, the composition comprising cryptospirolepine or pharmaceutically acceptable salt thereof is administered in combination with, prior to, concurrent with or subsequent to the administration of a therapeutically effective dose of a compound selected from the group consisting of chloroquine, hydroxychloroquine, mefloquine and pharmaceutically acceptable acid addition salts thereof.

BRIEF DESCRIPTION OF THE DRAWINGS

FIG. 1A is a partial expansion of FIG. 1B.

FIG. 4 is the COSY spectrum of the aromatic region of the proton NMR spectrum of cryptospirolepine in $d_6$-DMSO.

FIG. 6A is the HMBC spectrum of cryptospirolepine in $d_6$-DMSO (F1). The spectrum was at 500 MHz with the long-range delay optimized for 10 Hz (50 msec) and the low-pass J-filter set for an average one-bond coupling constant at 165 Hz. Aliphatic carbon resonances including the N-methyls and the spiro-quaternary carbon resonances are excluded from the spectrum. Additionally, no long range correlates were observed for amide carbonyl carbon resonance. FIG. 6B is a plot of the HMBC spectrum from F1 and F2. FIG. 6C is the HMBC spectrum (F2).

FIG. 8A is the ROESY spectrum of cryptospirolepine [2] in $d_6$-DMSO recorded at 500 MHz with a mixing time of 250 msec using a 3 KHz spinlocking field. FIG. 8B is a plot of the ROSEY spectrum in $d_6$-DMSO (F1 and F2). FIG. 8C is the ROSEY spectrum (F2). The data were acquired in a hypercomplex mode using the States-Haberkorn method.

DETAILED DESCRIPTION OF THE INVENTION

Figure 1A:
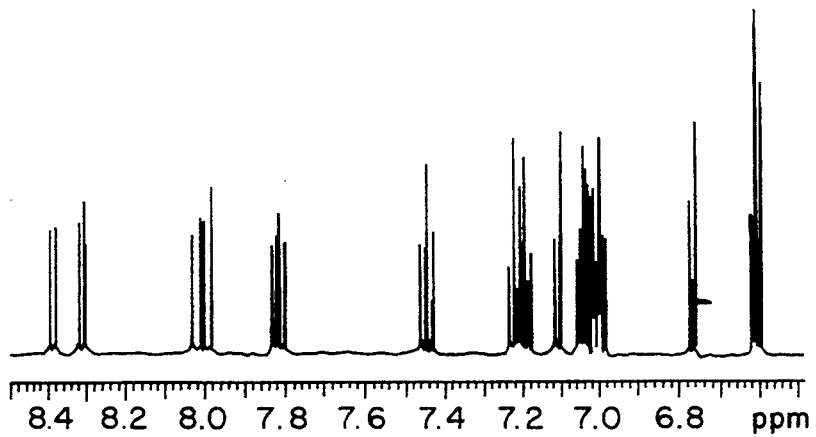
FIGS. 1A and 1B shows the proton NMR spectrum of cryptospirolepine. The spectrum contains resonances for a NH at 10.67 ppm, 17 vinyl/aromatic protons, and two N-methyl groups (4.37 and 3.94 ppm).

The present inventors have been involved in research to identify compounds useful in the treatment of falciparum malaria. This research has led to the study of extracts of West African plants including *Cryptolepis sanguinolenta* (Lindl.) Schlecter, which have been used in folk medicine by native herbalists to treat various ailments including upper respiratory infections, urinary tract infections and malaria.

Evidence has shown that extracts of the Cryptolepis plant have antimalarial activity, however, the component or components responsible for the antimalarial activity has been heretofore unknown. In view of the evidence of antimalarial activity of plant extracts, the present inventors have attempted to purify and identify the responsible compounds.

Four alkaloids were purified from *C. sanguinolenta* root extracts. A specific component of the root extracts that is responsible for at least part of the antimalarial activity has been purified and identified as the novel compound, cryptospirolepine. Cryptospirolepine was purified from an ethanolic extract of dried powdered *C. sanguinolenta* roots by standard partitioning methods, as well as column and preparative thin layer chromatography.

Cryptospirolepine is an indoloquinoline-indolobenzazepine spiro-nonacyclic dimeric alkaloid. The structure of the compound was determined by a series of two-dimensional NMR experiments including COSY, NOSEY, inverse-detected heteronuclear chemical shift correlation (HMQC) and long-range inverse-detected heteronuclear chemical shift correlation (HMBC). Cryptospirolepine has the following structure:

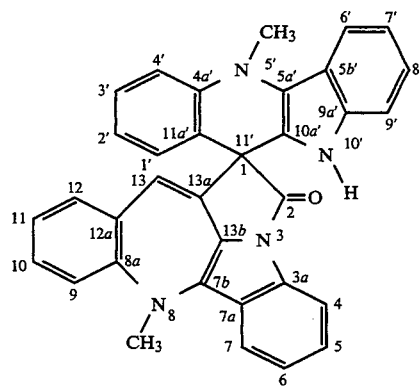

The structure of cryptospirolepine shows it to be an entirely novel spiro-nonacylic alkaloid related to and possibly biosynthetically derived from cryptolepine, another alkaloid purified from *C. sanguinolenta* root extracts.

The mechanism by which cryptospirolepine exhibits its antimalarial activity has not yet been elucidated. However, it has been demonstrated that cryptospirolepine is effective in vitro against well-characterized clones of *Plasmodium falciparum* malaria parasites. Cryptospirolepine offers another approach to the prevention and treatment of malaria, which is sorely needed in view of the resistance of *Plasmodium falciparum* to multiple known antimalarial drugs.

Cryptospirolepine is useful as an active ingredient in antimalarial compositions in the form of the spiro-nonacyclic alkaloid and as the pharmaceutically acceptable salt thereof.

The compounds of the present invention are most easily administered in the form of a pharmaceutically acceptable non-toxic acid addition salt formed from cryptospirolepine and an organic or inorganic acid recognized in the art. Examples of such acid addition salts include acetate, aspartate, benzoate, benzenesulfonate, bisulfate, butyrate, citrate, dihydrogen phosphate, dodecylsulfate, ethanesulfonate, hydrochloride, hydrobromide, hydroiodide, lactate, methanesulfonate, succinate, sulfate, tartrate, thiocyanate, maleate, fumarate and the like. Preferably, cryptospirolepine is administered as the hydrochloride salt.

For the prevention or treatment of infection with *Plasmodium falciparum* a composition of the present invention may be administered which contains other antimalarial agents, such as, for example, cryptolepine, cryptolepine-HCl, chloroquine, mefloquine, quinine, hydroxychloroquine, amodiaquine, quinidine pyrimethamine, artemisinin or sulfadoxine. Other antimicrobial agents or antipyretic agents, such as acetaminophen (paracetamol) may also be incorporated into the cryptospirolepine composition.

Cryptospirolepine containing compositions may be administered to a patient in need of the treatment or prevention of malaria in combination with, prior to, concurrent with or subsequent to the administration of another antimalarial agent, such as for example, quinine, chloroquine, mefloquine, or cryptolepine, an antipyretic compound, such as, for example, acetaminophen (paracetamol) or an antimicrobial agent, such as, for example, an antibiotic.

The composition of the present invention may be administered, alone or in combination with other agents for the treatment of the symptoms of malaria orally, parenterally or rectally, in dosage unit formulations containing conventional non-toxic, pharmaceutically acceptable carriers, adjuvants and vehicles.

The compositions of the present invention can be used in the form of a pharmaceutical preparation, for example, in solid, semisolid or liquid form, which contains cryptospirolepine and/or the acid addition salt thereof, as an active ingredient, alone or in combination with other antimalarial, antimicrobial or antipyretic compounds, in admixture with an organic or inorganic carrier or excipient suitable for enteral or parenteral administration. Cryptospirolepine may be compounded, for example, with pharmaceutically acceptable carriers for tablets, pellets, capsules, suppositories, solutions, emulsions, suspensions or any other form suitable for use. Suitable carriers include for example, water, glucose, lactose, gum acacia, gelatin, mannitol, starch paste, talc, keratin, colloidal silica, urea and the like. In addition auxiliary, stabilizing, thickening and coloring agents may be used. Cryptospirolepine is present in the compositions in an amount sufficient to produce the desired effect upon the process of the malarial disease, such as the prevention of the disease in a person exposed to the malarial parasite or the complete inhibition of the life cycle of the malarial parasite within the patient suffering from malaria.

The compositions of this invention may be administered by a variety of methods including orally, intramuscularly, intravenously or subcutaneously. The preferred mode of administration is through the oral mode, however, the precise mode of administration is left to the discretion of the practitioner.

Compositions for oral administration may be in the form of tablets, troches, lozenges, aqueous or oily suspensions, granules or powders, emulsions, capsules, syrups or elixirs. Orally administered compositions may contain one or more agents, such as, sweetening agents such as sucrose and lactose, flavoring agents such as peppermint, oil of wintergreen or cherry, coloring agents and preserving agents to provide a pharmaceutically palatable preparation. Moreover, compositions in tablet form may be coated to delay disintegration and absorption in the gastrointestinal tract thereby providing a sustained action over an extended period of time. A time delay material such as glycerol monostearate or glycerol stearate may be used.

Aqueous suspensions containing cryptospirolepine may also contain one or more preservatives, such as, for example, ethyl or n-propyl-p-hydroxy-benzoate, one or more coloring agents, flavoring agents or sweetening agents.

The dosage of the present compositions for treatment or prevention of malaria depends on the route and frequency of administration, as well as the age, weight and physical condition of the patient. The appropriate dosage of the compositions can be readily determined by the skilled medical practitioner.

The following examples are included to illustrate the use of the compounds of this invention in the treatment or prevention of malaria. These examples are exemplary only and are not intended to limit the invention in any way.

EXAMPLE 1

Extraction and Isolation of Cryptospirolepine

Powdered, oven-dried (60° C.) roots of *C. sanguinolenta* (1 kg) were defatted with petrol for 12 hours. The marc was extracted by percolation with ethanol (80%, 10×10 liter). The ethanol was evaporated in vacuo at 40° C. The extract residue was mixed with acetic acid (10%, 500 ml), diluted with water (500 ml) and allowed to stand overnight after which the mixture was filtered through Whatman No. 2 paper (filtrate A). Insoluble material obtained from filtering was dissolved in a minimum amount of ethanol, treated with acetic acid (10%, 200 ml), and diluted with water until resinous material failed to precipitate. The resulting mixture was filtered on Whatman No. 2 paper and the filtrate (filtrate B) was added to filtrate A. The pH of the combined filtrates was adjusted to 9.5 with ammonium hydroxide and the filtrate extracted with chloroform (5×200 ml). The combined chloroform extracts were partitioned with water (1 liter), dried over anhydrous sodium sulfate, filtered and evaporated. 15 g. of alkaloid residue was obtained.

The alkaloid residue was dissolved in chloroform (50 ml), adsorbed onto alumina (20 g) and chromatographed over alumina (200 g, column A). Elution was carried out using petrolchloroform (1:2), followed by chloroform.

Elution of column A with chloroform (1 liter) resulted in a residue, which on treatment with absolute ethanol gave light brownish pink crystals of cryptospirolepine (40 mg). The crystals quickly charred on heating.

EXAMPLE 2

Characterization of Cryptospirolepine

The uv spectrum of cryptospirolepine showed maxima at 506 nm (log ε 4.44), 474 (4.19), 368 (4.38), 352 (sh) (4.27), 280 (4.65), 250 (4.80), 223 (sh) (4.75) and 215 (4.83), which was characteristic of an indoloquinoline alkaloid. The infrared spectrum (film-KBr) displayed a weak carbonyl absorption at 1612 cm$^{-1}$ and strong aromatic bands at 1588 and 1512 cm$^{-1}$. Infrared spectra were acquired using an FX6260 FTIR spectrophotometer (Analect) equipped with a model FXA-501 beam condenser (9x). The interferometer was operated at 2cm$^{-1}$ resolution and the infrared signal was detected using a broad band MCT (mercury-cadmium telluride detector).

The ir max (film —KBr) cm$^{-1}$ showed maxima at 1612, 1588, 1512, 1454, 1394, 1326, 1305, 1228, 1051, 1025, 1008 and 741.

Cryptospirolepine was analyzed in the solid state as a KBr pellet. Solutions were prepared for IR data acquisition by dissolving a sample of cryptospirolepine in d$_3$ acetonitrile, d$_4$-methanol: d$_3$ acetonitrile (2:3v/v) and d$_6$-DMSO. Spectra were obtained of these solutions in a micro-cavity KBr cell with a 0.1 mm (I.D.) cell path.

Figure 2:
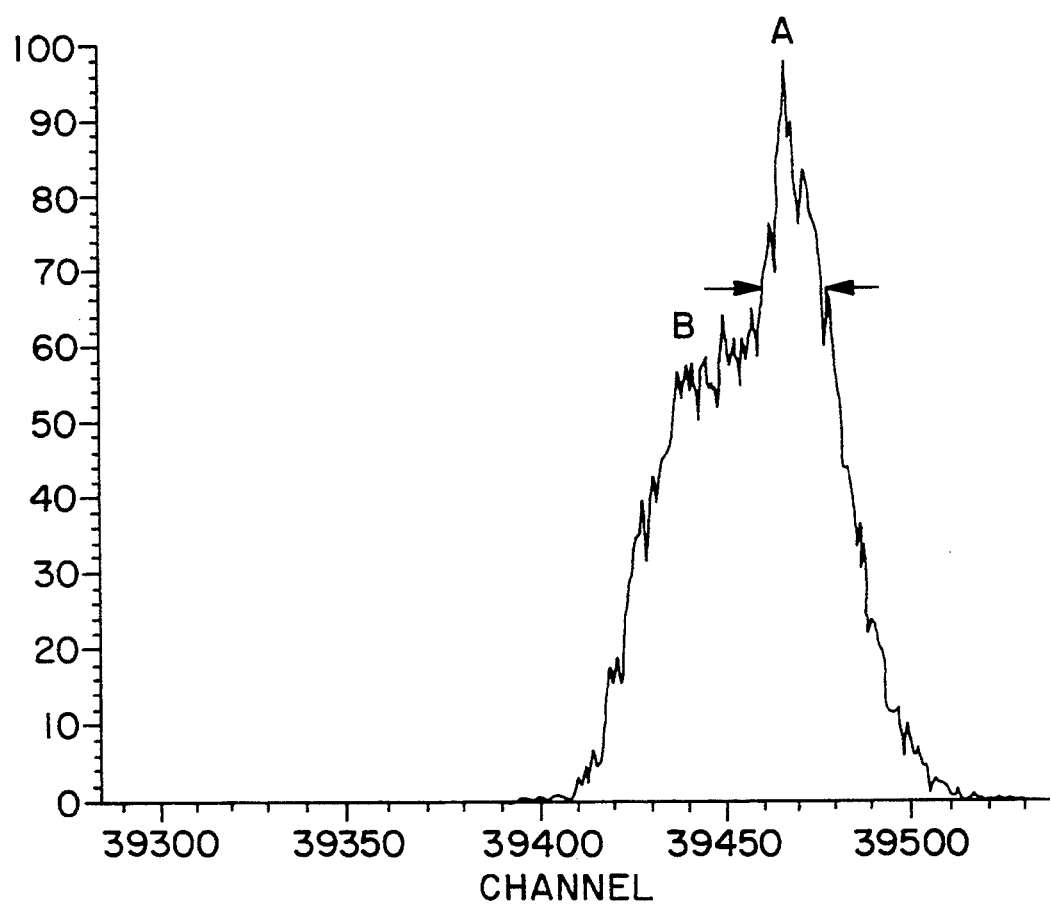
FIG. 2 is the carbon NMR spectrum of cryptospirolepine recorded in $D_6$-DMSO at 100.6 MHz.

A fast atom bombardment mass spectrum (FAB mass spectrum) was obtained of a sample of cryptospirolepine dispersed in a glycerol matrix and is shown in FIG. 2. The FAB mass spectrum of cryptospirolepine gave an (M+H)+ ion at m/z 505 and fragment ions between 230 and 275. The high resolution mass measurement of the ion at 505 Da was obtained using the method of Johnson and Taylor, Org. Mass Spectrum, 22, 807 (1987). The measured exact mass of 505.1989, corresponds to an empirical formula of C$_{34}$H$_{24}$N$_4$O with an error of −3.9 millimass units or to C$_{35}$H$_{24}$N$_2$O$_2$ with an error of +7.3 millimass units.

Figure 1B:
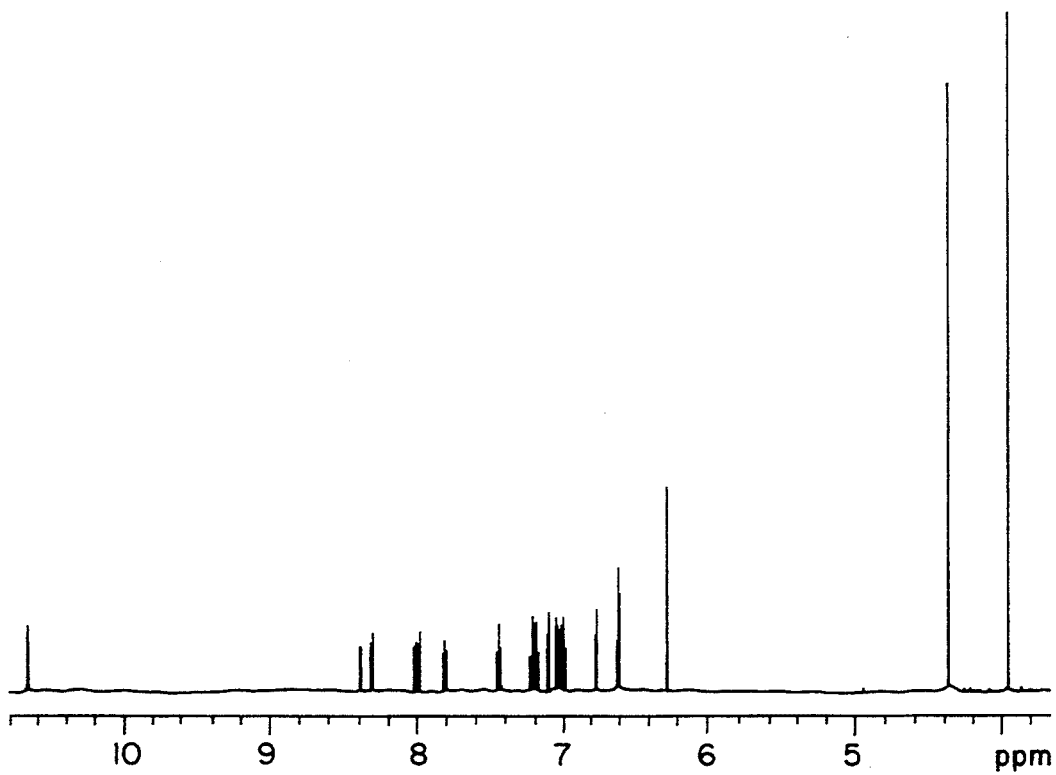
Figure 3A:
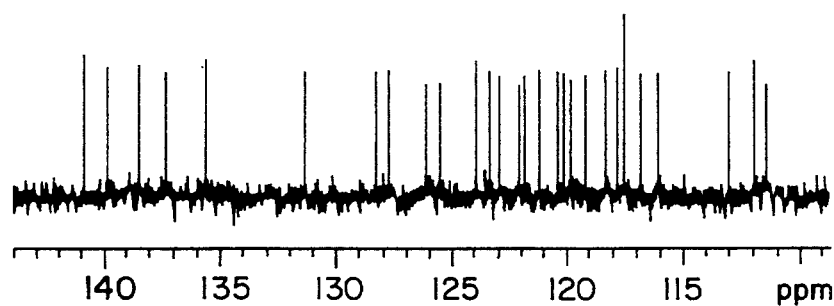
FIGS. 3A and 3B are an expansion of the aromatic region (bottom trace, FIG. 3B) and the CH only DEPT spectrum (top trace, FIG. 3A) of the carbon NMR spectrum of cryptospirolepine.
Figure 3B:
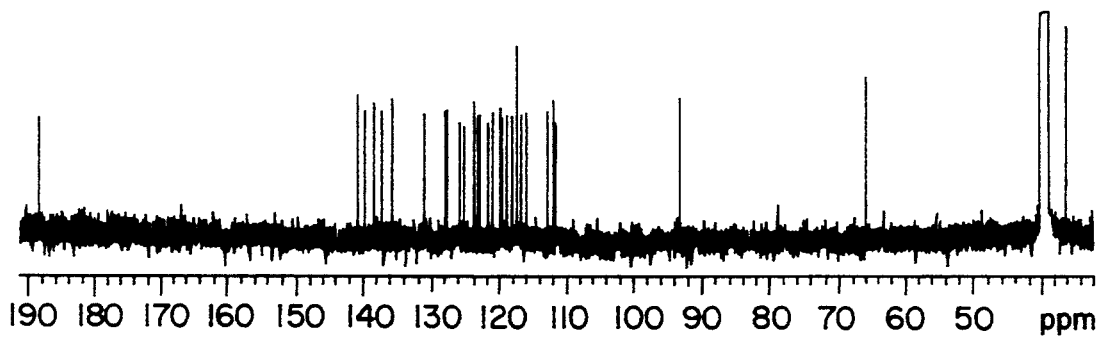
Figure 4A:
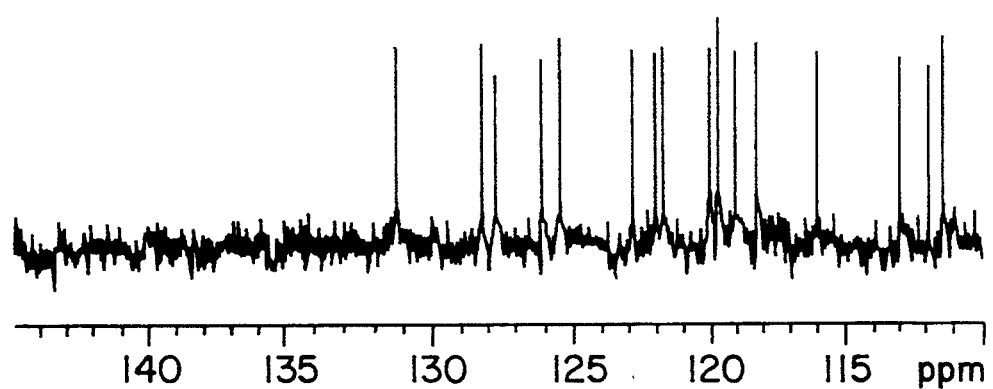
FIG. 4A is the methine (CH) only DEPT spectrum.
Figure 4B:
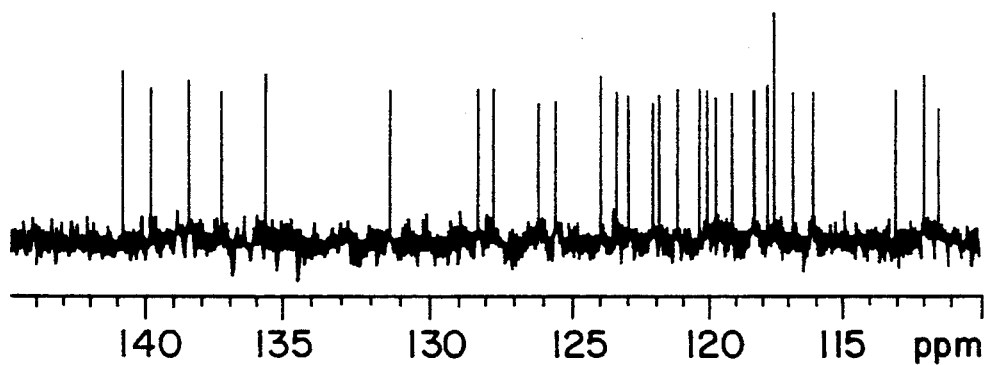
FIG. 4B shows the expansion of the aromatic/vinyl region of the 13° C. spectrum from 110–145 ppm.

The proton spectrum of cryptospirolepine gave resonances corresponding to 24 protons. The full proton NMR spectrum of cryptolepine is shown in FIGS. 1A and 1B. The spectrum contains resonances for a NH at about 10.67 ppm, resonances for 17 vinyl/aromatic protons and for two N-methyl groups, which resonate at 4.37 and 3.94 ppm. The full proton-decoupled carbon spectrum of cryptospirolepine is shown in FIG. 3. Thirty-four carbons were observed in the spectrum, 28 of them presumably vinyl or aromatic. The insert plotted above the full 13° C. spectrum shows all of the vinyl/aromatic carbon resonances except for the vinyl carbon resonating at 93.7 ppm. Based on the carbon spectrum and the number of proton resonances, the empirical formula of the compound was fixed at C$_{34}$H$_{24}$N$_4$O. FIG. 4B shows the expansion of the aromatic/vinyl region of the 13° C. spectrum from 110–145 ppm (bottom). The same spectral segment of the methine(CH) only DEPT spectrum is plotted in the upper trace. Resonances absent from the top trace from the DEPT experiment are thus, identified as non-protonated quaternary vinyl/aromatic carbon resonances.

Figures 5A, 5B:
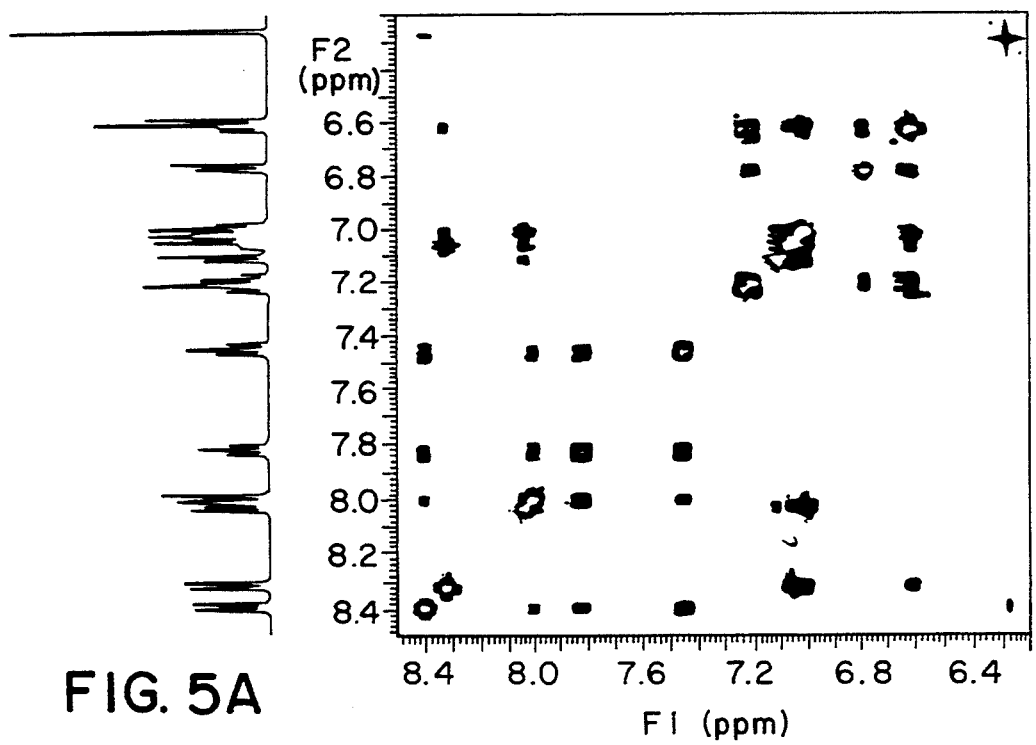
FIG. 5A is the HMQC spectrum of the aromatic region of cryptospirolepine in $d_6$-DMSO. The N-methyl resonances are excluded from the plot shown in FIG. 5B.
Figures 7A, 7B, 7C:
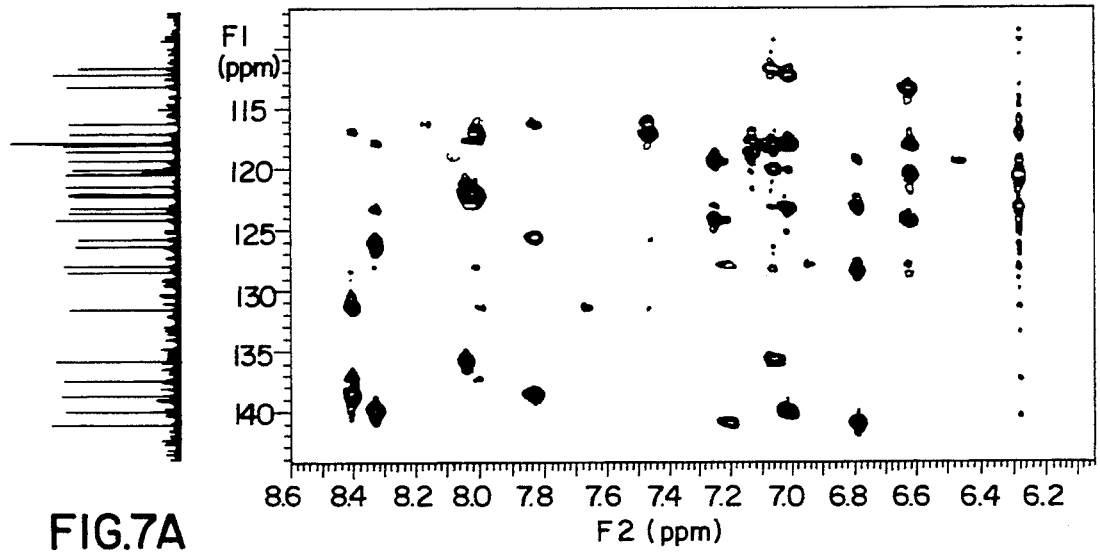
FIG. 7A is the ROSEY spectrum of cryptospirolepine in $d_6$-DMSO (F1) recorded at 500 MHz with a mixing time of 250 msec using a 3 KHz spin-locking field.
FIG. 7B is a plot of the ROSEY spectrum (F1 and F2).
FIG. 7C is the ROSEY spectrum (F2). The data were acquired in hypercomplex mode using the States-Haberkorn method.

The COSY spectrum (FIG. 5) encompassing 17 proton resonances ranging from 6.27–8.40 ppm showed four four-spin systems, which were expanded into more meaningful structural fragments through the interpretation of data from several two-dimensional nmr experiments, including HMQC (inverse-detected heteronuclear chemical shift correlation) (FIG. 6), HMBC (long-range inversed detected heteronuclear correlation) (FIG. 7) and ROSEY (FIG. 8). Proton-proton interactions from the COSY spectrum were used to partially establish the identities of the four-spin homonuclear systems. Carbon resonances directly attached to each of the identified protons were identified from the HMQC spectrum (FIG. 6). Where congestion in the proton NMR spectrum precluded the uequivocal identification of the complete four-spin system, homonuclear connectivity information was garnered form an HMQC-TOCSY spectrum. The component atoms of the four structural fragments were linked to quaternary carbons using long-range heteronuclear correlations from the HMBC spectrum shown in FIG. 7. Other long-range heteronuclear correlations, in conjunction with through space roe connectivities from the ROESY spectrum (FIG. 8) allowed the deduction of the final molecualr structure. The interpretation of the mass spectral and infrared data, in conjunction with the one- and two-dimensional NMR data are consistent with the structure.

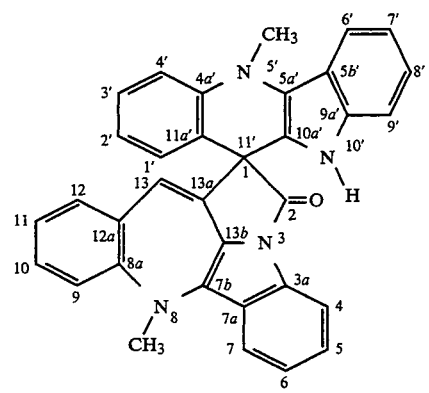

EXAMPLE 3

Antimalarial Activity of Cryptospirolepine

Figure 9:
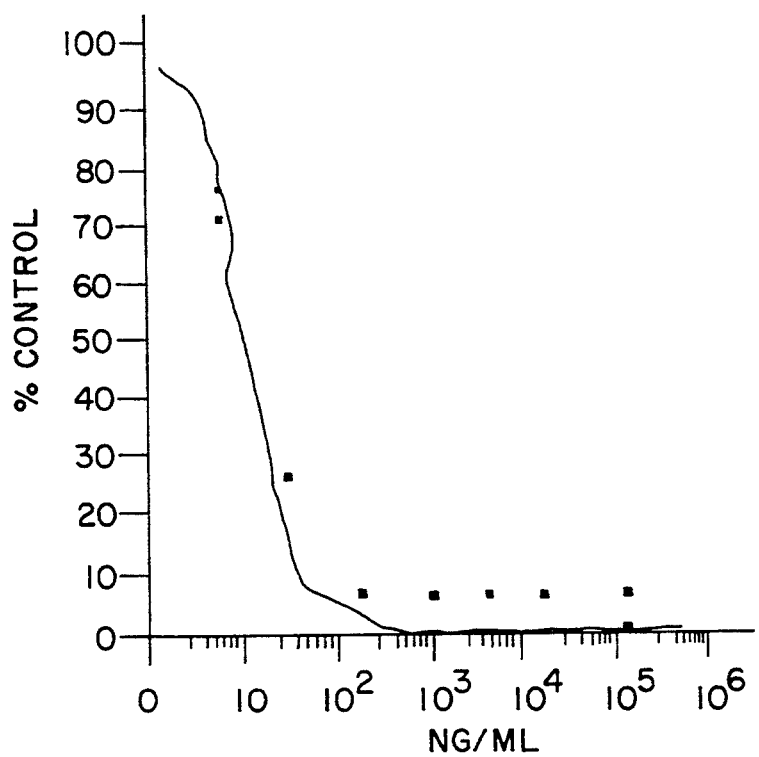
FIG. 9 is a graph of the inhibition of growth of plasmodium falciparum clone W-2 by concentrations of cryptospirolepine.
Figure 10:
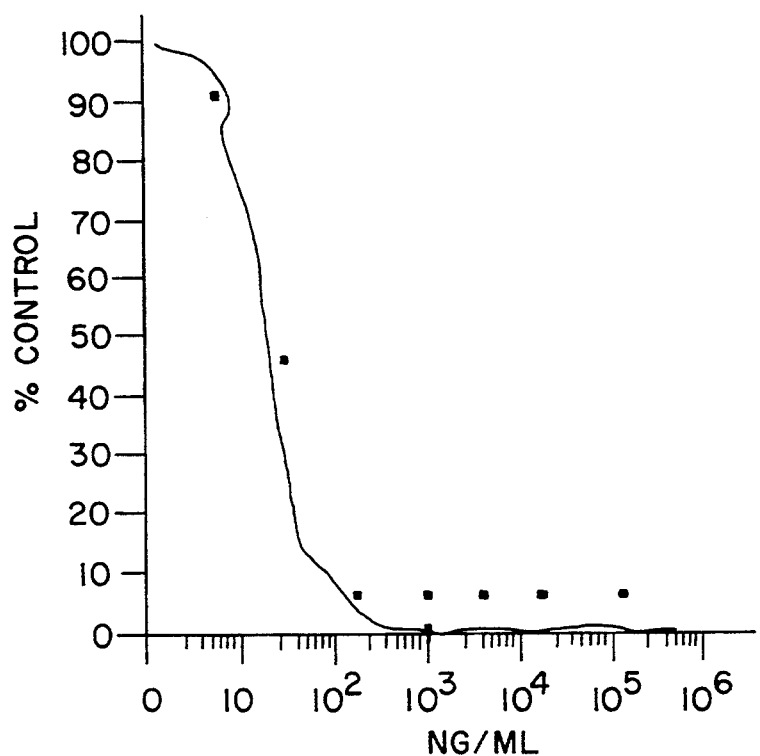
FIG. 10 is a graph of the inhibition of growth of plasmodium falciparum clone D-6 by concentrations of cryptospirolepine.

Cryptospirolepine was analyzed to determine the IC$_{50}$, the median concentration of the alkaloid which effectively inhibits the growth of 50% of the test organisms exposed to it within a stated period of time. Two independent clones of *Plasmodium falciparum*, D-6 and W-2, were used for testing. As controls, the IC$_{50}$ of quinine, mefloquine and chloroquine were also determined. The results are shown in Table I and the data are graphically illustrated in FIGS. 9 and 10.

TABLE 1

|  | W-2 Clone | D-6 Clone |
| --- | --- | --- |
| cryptospirolepine | 14.84 | 32.2 |
| quinine | 29.85 | 10.0 |
| chloroquine | 29.81 | 1.17 |
| mefloquine | 0.57 | 3.52 |

*units are ng/ml

These results show that cryptospirolepine is effective in killing *Plasmodium falciparum*, the organism responsible for malaria.

What is claimed is:

1. A compound of the formula

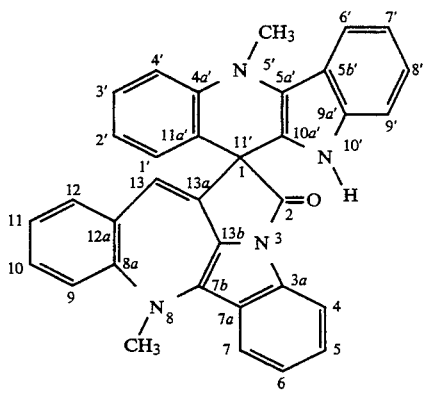

or a pharmacologically acceptable salt thereof.

2. The compound of claim 1 which is in the form of HCl salt.

3. An antimalarial composition comprising a therapeutically effective amount of the compound of the formula or its pharmacologically acceptable salt as set forth in claim 1 and a pharmaceutically acceptable carrier.

4. The antimalarial composition of claim 3 wherein the compound is the HCl salt of cryptospirolepine.

5. The antimalarial composition of claim 3 further comprising an additional pharmacologically active agent selected from the group consisting of other antimalarial agents, antibacterial agents and antipyretic agents.

6. The antimalarial composition of claim 3 further comprising a therapeutically effective amount of acetaminophen (paracetamol).

7. The antimalarial composition of claim 3 further comprising a therapeutically effective amount of cryptolepine.

8. The antimalarial composition of claim 7 wherein the cryptolepine is in the form of an HCl salt.

9. The antimalarial composition of claim 8 wherein the compound of the formula is in the form of HCl salt.

10. A method for treating malaria comprising the administration of a therapeutically effective amount of a composition comprising a therapeutically effective amount of cryptospirolepine or pharmacologically acceptable salt thereof to a patient who might be exposed to or is suffering from malaria.

11. The method for treating malaria according to claim 10 wherein the composition comprises a therapeutically effective amount of cryptospirolepine-HCl.

12. The method for treating malaria according to claim 10 wherein the composition further comprises a pharmacologically active compound selected from the group consisting of other antimalarial agents, antibacterial agents and antipyretic agents.

13. The method for treating malaria according to claim 10 wherein the composition is in tablet form for oral administration.

14. The method for treating malaria according to claim 10 wherein the composition is administered daily.

15. The method for treating malaria according to claim 10 wherein the cryptospirolepine is administered in combination with, prior to, concurrent with or subsequent to the administration of a therapeutically effective dose of a compound selected from the group consisting of chloroquine, hydroxychloroquine, amodiaquine, mefloquine, quinine, quinidine and pharmaceutically acceptable acid addition salts thereof.

* * * * *